US005731157A

United States Patent [19]
Miller et al.

[11] Patent Number: 5,731,157
[45] Date of Patent: Mar. 24, 1998

[54] TWO-SITE ALLERGEN IMMUNOASSAY

[75] Inventors: Larry S. Miller, Columbus; Balwant S. Bhullar, Westerville; Richard S. Tuttle; Victor S. Moore, both of Columbus, all of Ohio

[73] Assignee: The Procter and Gamble Company, Cincinnati, Ohio

[21] Appl. No.: 175,715

[22] Filed: Dec. 30, 1993

[51] Int. Cl.$^6$ .................................................. G01N 33/573
[52] U.S. Cl. ................................ 435/7.4; 34/80; 34/82; 34/472; 34/477; 435/7.9; 435/7.94; 435/963; 436/518; 436/531; 436/808; 436/826
[58] Field of Search ............................... 34/80, 92, 292, 34/294, 298, 299, 300, 82, 467, 472, 473, 474, 475, 476, 477, 480; 435/7.4, 7.9, 7.94, 289, 290, 291, 963; 436/518, 531, 808, 809, 826; 422/63, 67

[56] References Cited

U.S. PATENT DOCUMENTS

| | | | |
|---|---|---|---|
| 3,593,498 | 7/1971 | Semon | 55/267 |
| 3,902,971 | 9/1975 | Fletcher et al. | 195/103.5 R |
| 4,251,923 | 2/1981 | Kuri | 34/80 X |
| 4,256,697 | 3/1981 | Baldwin | 422/104 |
| 4,358,424 | 11/1982 | Weber et al. | 422/68 |
| 4,453,955 | 6/1984 | Cullen et al. | 55/387 |
| 4,545,958 | 10/1985 | Dopatka | 422/102 |
| 4,560,647 | 12/1985 | Stocker | 435/5 |
| 4,661,128 | 4/1987 | Bachhofer et al. | 55/208 |
| 4,670,405 | 6/1987 | Stetter et al. | 436/151 |
| 4,690,890 | 9/1987 | Loor et al. | 435/7.94 |
| 4,777,021 | 10/1988 | Wertz | 435/101 |
| 4,780,285 | 10/1988 | Kuypers et al. | 422/102 |
| 4,822,732 | 4/1989 | Sandström et al. | 435/6 |
| 4,851,357 | 7/1989 | Yamashina | 436/528 |
| 4,931,402 | 6/1990 | Abplanalp | 435/291 |
| 5,038,852 | 8/1991 | Johnson et al. | 165/12 |
| 5,063,090 | 11/1991 | Wannlund | 427/384 |
| 5,073,346 | 12/1991 | Partanen et al. | 422/99 |
| 5,110,551 | 5/1992 | Michal | 422/58 |
| 5,149,634 | 9/1992 | Bradley | 435/29 |
| 5,183,740 | 2/1993 | Ligler et al. | 435/7.32 |
| 5,187,084 | 2/1993 | Hallsby | 435/91 |
| 5,266,272 | 11/1993 | Griner et al. | 422/104 |

OTHER PUBLICATIONS

Cole–Parmer Instrument company Product Catalog 1991/1992, p. 219.

Frank et al., "Automation of DNA Sequencing Reactions and Related Techniques: A Workstation for Micromanipulations of Liquids"; *Biotechnology*, vol. 6, pp. 1211–1213 (1988).

Godfrey, T. et al., "Comparison of Key Characteristics of Industrial Enzymes by Type and Source." in: Godfrey, *Industrial Enzymology* (England, MacMillan Ltd., 1983), pp. 466–502.

Dambmann, C., et al. "How Enzymes Got Into Detergents." *Developments in Industrial Microbiogly*, vol. 12, (1971), pp. 11–23.

Dambmann, C. et al. "The Variety of Serine Proteases and Their Industrial Significance." in: Turk et al., *Proteinases and Their Inhibitors* (New York, Permagon Press, 1981), pp. 231–244.

Flindt, M. H. L., "Pulmonary Disease Due to Inhalation of Derivatives of *Bacillus subtilis* Containing Proteolytic Enzyme." *The Lancet*, (1969), pp. 1177–1181.

Pepys, J. et al., "Allergic Reactions of the Lungs to Enzymes of *Bacillus subtillis*." *The Lancet*, (1969), pp. 1181–1184.

Gilson, J. C. et al., "Biological Effects of Proteolytic Enzyme Detergents." *Thorax*, vol. 31, (1976), pp. 621–631.

Dunn, E. et al., "The Use of NN'–Dimethylcasein in the Determination of Proteolytic Enzymes in Washing Products and Airborne Dust Samples." *Analyst* vol. 96, (1971), pp. 159–163.

Rothgeb, T. M. et al., "The Raw Material, Finished Products, and Dust Pad Analysis of Detergent Proteases Using a Small Synthetic Substrate." *Journal Americal Oil Chemists' Society*, vol. 65, (1988), pp. 806–810.

Miller, L. S., et al., "Inhibition Enzyme Immunoassay for the Detection of Airborne Detergent Enzymes Causing Occupational Allergy." *Developments in Industrial Microbiology*, vol. 31 (1990), pp. 213–219.

Lowry O. H., et al., "Protein Measurement with the Folin Phenol Reagent." *Journal of Biological Chemistry*, vol. 193, (1951) pp. 265–275.

Peters, T., "Serum Albumin." in: Anfinsen, B. et al., *Advances in Protein Chemistry*, vol. 37, (New York, Academic Press, 1985), pp. 161–245.

Claeyssens, M., "The Use of Chromophoric Substrates and Specific Assays in the Study of Structure–Activity Relationships of Cellulolytic Enzymes." in: Aubert, J. P. et al., *Biochemistry and Genetics of Cellulose Degradation* (New York, Academic Press, 1988), pp. 393–397.

(List continued on next page.)

*Primary Examiner*—Paula K. Hutzell
*Assistant Examiner*—Susan C. Wolski
*Attorney, Agent, or Firm*—Philip J. Pollick

[57] ABSTRACT

An allergen immunoassay method features the use of a combination of a) closely controlled 1) elevated temperatures for assay reactions, 2) low temperatures for reagents and samples, 3) times for assay steps and especially assay reaction times, 4) reagent concentrations, and 5) reagent amounts; b) the use of a fast and accurate method of sample preparation that removes dust and contaminants; c) the stabilization of samples to avoid auto- and antibody degradation and unwanted effects of sample contaminants; and d) the formation of a colored product to determine the amount of a specific allergen. This combination provides an assay that can be completed in a few hours while retaining the precision, accuracy, sensitivity and response curve of previous methods requiring much longer periods of time. The assay is especially suitable for computer control using a robotic liquid distribution system and allows for the determination of four different specific allergens in one hundred sixty samples in duplicate with standards and controls in an eight hour period with a significant reduction in the number of steps and attended technician time over previous assays.

32 Claims, 9 Drawing Sheets

OTHER PUBLICATIONS

American Conference of Governmental Industrial Hygienists (ACGIH). *Documentation of Threshold Limit Values.* Fourth edition, Cincinnati, Ohio, (1980) pp. 374–375.

Agarwal, M. K. et al. "Immunochemical Quantitation of an Airborne Proteolytic Enzyme, Esperase®, In a Consumer Products Factory." *American Industrial Hygeiene Association Journal*, vol. 47. No. 2 (1986), pp. 138–143.

Swanson, M. C. et al. "Immunochemical Quantification and Particle Size Distribution of Airborne Papain in a Meat Portioning Facility." *American Industrial Hygiene Association Journal*, vol. 53, No. 1 (1992), pp. 1–5.

Voller, A. et al., "Enzyme Immunoassays with Special Reference to ELISA Techniques." *Journal of Clinical Pathology*, vol. 31 (1978), pp. 507–520.

Wells, J. D. et al., "Detection of Airborne Industrial Papain by a Radioimmunoassay." *American Industrial Hygiene Association Journal*, vol. 42, Apr. (1981), pp.321–322.

Chien, P. T. "The Development of a Fluorometric Method for the Assay of Subtilisins." *American Industrial Hygiene Association Journal*, vol. 39, Oct. (1979), pp. 808–816.

Fulwiler, R. D. et al., "Evaluation of Detergent Enzymes in Air." *American Industrial Hygiene Association Journal*, Apr. (1972), pp. 201–211.

Hendricks, M. H. "Measurement of Enzyme Laundry Product Dust Levels and Characterisitcs in Consumer Use." *Journal of the American Oil Chemists' Society*, Jun. (1970), pp. 207–211.

Paixao, L. M. et al., "Automated Bioassay of Proteolytic Enzymes in Detergents" *Journal of the American Oil Chemists' Society*, Oct. (1969), pp. 511–514.

Markland, F. S. et al., "Subtilisins: Primary Structure, Chemical and Physical Properties" in: Boyer, P. D., *The Enzymes*, vol. 3, (New York Academic Press, 1971), pp. 561–608.

Waller, M. "The Hydrolysis of Human IgG with Subtilisin" *American Journal of Clinical Pathology*, vol. 31, (1975), pp. 358–364.

Data Index 5, "Current Industrial Enzyme Assays and Unit Definititions" in: Godfrey and Reichelt, *Industrial Enzymology*, (England, MacMillan Ltd., 1983), pp. 553–557.

Agarwal, M. K., et al., "An Immunochemical Method to Measure Atmospheric Allergens" *Journal Allergy and Clinical Immunology*, vol. 68, No. 3, (1981), pp. 194–200.

Feder, J., et al. "Stabilization of Proteolytic Enzymes in Solution." *Biotechnology and Bioengineering*, vol. XX, (1978), pp. 1865–1872.

Friedman, S., et al. "Enzymic Activity of Proteases in Detergent Systems: Comparison of Assay Methods and the Role of Interfering Substances." *Journal of the American Oil Chemists' Society*, vol. 46, (1968), pp. 81–84.

Swisher, R. D., "Detergent Enzymes: Biodegradation and Environmental Acceptability." *Bioscience*, vol. 19, (1969), pp. 1093–1094.

Miller, L. S., et al. "Enzyme Imunoassay for the Quantitation of an Alkaline Protease in Airborne Samples." *U. S. Enviromental Protection Agency Res. Dev.*, (Rep.), EPA/600/D–89/189, EPA Date (1988).

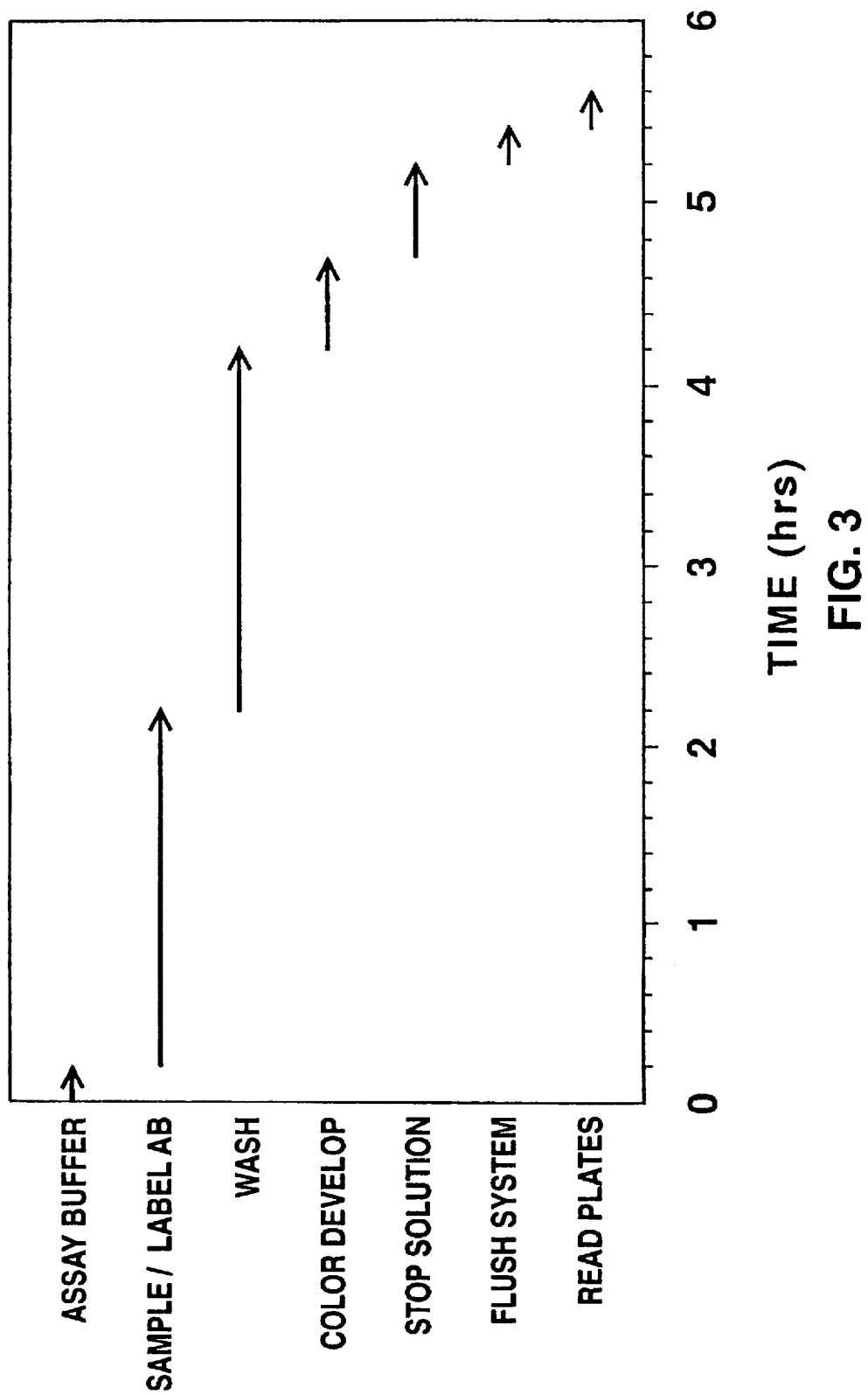

TO STEP 216 FIG. 7b

TWO-SITE ALLERGEN IMMUNOASSAY

BACKGROUND OF THE INVENTION

1. Field of the Invention

This invention relates to a method and means for detecting and quantifying allergens, especially airborne enzyme allergens by using especially a two-site immunoassay that produces a product with a measurable color change within a short time period.

2. Background Description

Many well-characterized allergens, e.g., mites, ragweed, and Alternaria, are enzymes.[1] The sulphydryl protease, papain, an extract of *Carica papaya*, is used in a wide variety of industrial and consumer products. This proteolytic enzyme is used as an additive in foods, drugs, and cosmetics, in the tanning and brewing industries, and as a meat tenderizer.[2] Microbial protease and nonprotease enzymes are commonly added to detergent products to enhance cleaning efficiency.[3,4,5]

However, these materials can elicit allergic reactions in some individuals after exposure to these enzymes.[6,7,8,9,10] To avoid this problem, prilling or microencapsulation techniques have been developed to minimize airborne dust levels. The success of these techniques coupled with workplace control of airborne dust at detergent plants have led to low enzyme dust levels resulting in virtual elimination of allergenic symptoms among workers. In addition, enzyme assays have been developed for quantifying enzyme levels[11] and to assure compliance with The American Conference of Governmental Industrial Hygienists (ACGIH) standard of 60 ng enzyme/m$^3$ air.[12]

Typically these assays involve the enzyme-mediated digestion of a specified enzyme substrate.[13] For example, protease activity in air samples has been quantitated by an assay using protease digestion of casein or N,N'-dimethylcasein followed by the reaction of new free amino groups from enzyme-released peptides with trinitrobenzenesulphonic acid to produce colorimetrically detectable Meisenheimer complexes.[14] The newly formed amino groups have also been reacted with fluorescamine to form a fluorescent complex.[15] The casein and N,N'-dimethylcasein colorimetric methods have been established by the detergent manufacturing industry as standard procedures for determining these enzymes[16,17] and an automated system for the reaction of proteolytic enzymes with casein has been described.[18]

Recently, a simpler assay using the chromogenic substrate, N-succinyl-L-alanyl-L-alanyl-L-prolyl-L-phenylalanyl p-nitroanalide has been presented.[19] In this assay, enzyme action on the substrate cleaves the phenylalanyl p-nitroanalide amide bond directly yielding the yellow chromophore, p-nitroaniline. Quantitation follows directly from the measurement of absorbance of the enzyme released yellow chromophore rather than a subsequent reaction of the enzyme released amine with a reagent to produce a colorimetrically detectable complex.

However, there are many problems with detecting enzyme allergen levels by these methods. Enzymes have been known to react with themselves in an autodegradative reaction resulting in fragments that are enzymatically inactive but maintain their allergenic properties.[20] It is also known that enzymes can degrade antibodies.[21] Enzyme activity is also modulated by components in detergent products.[22] Environmental sources contain microorganisms that also can contribute enzymes to the samples.[23] Oxidizing agents in the sample can inhibit enzyme activity. Certain nitrogen-containing compounds such as amino acids and ammonia and certain metal ions such as iron may interfere with the casein and modified casein procedure by formation of colored products with trinitrobenzene sulfonic acid.[24] Furthermore, these methods can be used for quantitation only if air samples contain a single detergent enzyme because of the significant variation in rate constants of enzymes for a substrate.[25]

In 1981, Agarwal et al[222, 26] used a radioallergosorbent inhibition test for atmospheric allergens in which a solid phase allergen was prepared and reacted with plasma from subjects highly allergic to the studied allergens using a radiochemical inhibition scheme. It was noted that allergenic activity measured by the method could represent the contribution of several cross-reacting genera. Wells[27] used a radioallergosorbent test to detect the amount of airborne papain in an industrial setting. A papain containing sample was insolubilized and reacted with serum from a papain sensitized human which in turn was reacted with radioactive iodine labeled rabbit antibody specific for human serum IgE. The reactions were carried out at room temperature and the assay took at least 24 hours. Agarwal[28] developed an immunochemical system for quantitation of airborne proteolytic enzymes in a bleach factory. Crude rabbit antibodies for an enzyme were insolubilized in a microwell, reacted with an enzyme containing sample which in turn was reacted with highly-purified, radioactive-iodine-labeled, rabbit antibodies specific for the enzyme. Sample preparation and reactions were all carried out at 4° C. and took at least 30 hours. Phenylmethylsulfonyl fluoride was used to inhibit enzyme sample auto- and antibody degradation. Using a similar radiometric method, Swanson[29] determined the activity of papain. Sample preparation was carried out at 4° C. and the reactions run at room temperature with the assay taking at least 36 hours. Glycerol and iodoacetate were used to control the enzymatic activity of the papain samples. Swanson noted that variability among replicate assays might be as much as 100% as a result of compounding errors at any or all of the handling steps but that typically the variability should not exceed 50% if replicate assays are performed by using the same reagents within a reasonable time period.

The above radioassays have many disadvantages. In particular, there are radiation hazards in handling and disposing of the radioactive materials used in the tests. The short half-life of many of the radioactive isotopes give rise to transport problems between the manufacturer and the laboratory as well as reagent shelf life. Finally expensive equipment is required to measure radioactivity. As a result, an effort has been made to find an allergen analysis method that avoids the risks associated with radioactive materials.

To this end, Miller et al[30] have recently used an inhibition colorimetric enzyme analysis. Purified enzyme was insolubilized in a microwell; diluted rabbit antibody for the proteolytic enzyme was incubated with a sample containing the enzyme, added to the microwell, reacted, and removed; an alkaline phosphatase/goat anti-rabbit immunoglobulin conjugate added, incubated, and excess conjugate removed; a chromogenic substrate (p-nitrophenylphosphate) added, reacted, and stopped; and the amount of colored product produced determined. Sample preparation and sample/antibody conjugates were prepared at 4° C. while other reactions were carried out at room temperature. The assay required numerous manual steps and 28 hours elapsed time to complete.

SUMMARY OF THE INVENTION

It is an object of this invention to reduce the elapsed time of an allergen assay to a time period of a few hours. It is a further object of this invention to provide a fast and efficient method of stabilized allergen recovery from a sample source. It is an object of this invention to give a highly accurate, precise and reproducible assay. It is an object of this invention to provide a simple method of assay that can be easily automated and avoids manual intervention. It is a further object of this invention to avoid the non-specificity of previous test methods and provide a highly specific method to determine a specific allergen. It is an object of this invention to avoid enzyme auto- and antibody degradation. It is an object of this invention to avoid unwanted assay effects of non-assayed sample components. It is an object of this invention to detect allergenic enzyme fragments especially when the fragments no longer have enzyme activity.

These and other objects of the invention are met through the use of an allergen assay method that features the use of a combination of closely controlled 1) elevated temperatures for assay reactions, 2) lowered temperatures for reagents and samples, 3) times for assay steps especially assay reactions, 4) reagent concentrations, and 5) reagent amounts; the use of a fast and efficient method of sample preparation that avoids dust and other contaminants; the stabilization of samples to avoid auto- and antibody degradation and unwanted effects of sample contaminants using nonspecific reagents; and the formation of a colored product to determine the amount of allergen. This combination of features has the advantage of providing an assay that can be completed in a few hours while giving a precision, accuracy, sensitivity and response curve comparable to previous methods requiring much longer time periods. The assay is particularly effective for allergens, especially airborne allergens such as enzymes including proteases such as detergent enzymes, carbohydrases, and oxidazes. These allergens include subtilisins, cellulase, Savinase, papain, α-amylase, trypsin, and chymotrypsin.

The assay method consists of the following steps. First a collected sample is eluted to obtain the suspected allergen (sample portion) in a liquid medium. This is done by placing a sample filter sheet in a sample tube with a reagent and slowly rotating the tube for about thirty minutes at room temperature. The sample portion is stabilized by providing a reagent with buffers, antioxidants, enzyme stabilizers, antimicrobial agents, and similar materials. Preferably the sample portion is eluted from the sample sheet with the stabilizing reagent. This not only stabilizes the sample portion but has been found effective in removing dust and contaminants such as non-enzyme detergent ingredients. The stabilized sample and all reagents prepared to meet assay concentration requirements are maintained at a temperature below room temperature, preferably at about 4°±1° C.

A reaction site, typically a microwell in a microwell plate, with an insolubilized substance is obtained by insolubilizing a substance, e.g., antibody, which specifically binds to a specific allergen to be determined. The microwell plate reaction sites are previously prepared and stored at 4°±1° C. until use.

A given amount of the chilled and stabilized sample is transferred to the reaction site and reacted with the insolubilized substance for a given time, usually 15 minutes at 37°±1° C., to bind a specific allergen to the insolubilized substance. A given amount of labeled substance is then transferred to the reaction site with the labeled substance being prepared prior to the assay by labeling a substance which specifically binds to the specific allergen (typically an antibody and usually the same antibody insolubilized previously at the reaction site) with a labeling agent. The labeled substance is reacted with the bound specific allergen for a given time (e.g., 135 minutes) at a temperature greater than room temperature (e.g., 37°±1° C.) to bind the labeled substance to the bound specific allergen. Unbound labeled substance is then removed from the reaction site and the amount of labeled substance bound to the specific allergen is determined. Typical labeling agents include radioisotope, enzyme, fluorescent, chemiluminescent, phosphorescent, and infra-red emitting materials.

Although the labeling agent could be a radioactive material which could be determined by counting, the use of radioactive materials presents problems which are preferably avoided. Rather, it is preferred that the labeling substance be an enzyme such as alkaline phosphatase and that the determination of the amount of labeled substance bound with the specific allergen is carried out by transferring a given amount of substrate such as p-nitrophenyl phosphate that reacts with the labeling enzyme to give a colored product. Other enzyme labeling agents include horseradish peroxidase, β-D-galactosidase, glucose oxidase, acetyl cholinesterase and urease. The substrate and enzyme are reacted for a given time (e.g., 30 minutes) and at temperature greater than room temperature (e.g., 37°±1° C.) to form a colored reaction product. The enzyme-substrate reaction is stopped as, for example, by adding ethylenediaminetetraacetic acid, to the reaction site and a property, such as color, of the reaction product, e.g., absorbance, is measured. The property of the colored product is compared with the same property of a colored product formed when known amounts of specific allergen are substituted for the sample portion to give the amount of specific allergen in the sample portion.

The method also features a unique desiccator that allows for the drying of microwell plates in a sealed chamber using desiccated, filtered and properly distributed circulating air in a closed loop at low temperature. This has the advantage of avoiding atmospheric and desiccant particle contamination of the plates and affords prolonged storage of the plates thereby avoiding the need to prepare fresh plates with each assay.

The method features the use of a combination of 1) a programmable computer for controlling the time and amounts of reagents and sample used in each assay step, 2) a sample and reagent distribution arm controlled by the computer for transferring controlled amounts of reagents and sample to a reaction site and removing materials from the reaction site; 3) a cooler for maintaining the sample and reagents at a given temperature below room temperature (room temperature being defined as 21°±1° C.); a heater for heating and maintaining the reaction site (and associated reactants and products) at a temperature above room temperature; and a reader used in determining the amount of allergen. This combination has the advantage of avoiding human intervention in many of the steps of the assay while providing controlled amounts of reagents and sample, cooled reagents, a heated reaction site and allows for the determination of four different allergens in one hundred sixty samples plus standards and controls carried out in duplicate within an eight hour period with a precision, accuracy, and sensitivity equivalent to the same number of manual assays requiring a much longer total elapsed time.

In summary, an allergen immunoassay method and equipment have been developed that give highly reliable and reproducible results with a significant reduction in the number of steps and attended technician time. This method and equipment are especially useful for the monitoring and analysis of air samples for the presence of allergens such as industrial enzymes in the consumer products, health care, food processing, and biopharmaceutical industries.

The foregoing and other advantages of the invention will become apparent from the following disclosure in which one or more preferred embodiments of the invention are described in detail and illustrated in the accompanying drawings. It is contemplated that variations in the methods, procedures, structural features and arrangement of components may appear to a person skilled in the art without departing from the scope of or sacrificing any of the advantages of the invention.

BRIEF DESCRIPTION OF THE DRAWINGS

FIG. 3 is a timing schedule for an automated allergen immunoassay in which one-hundred sixty samples with four different enzymes plus standards and controls are analyzed in duplicate.

Figure 1:
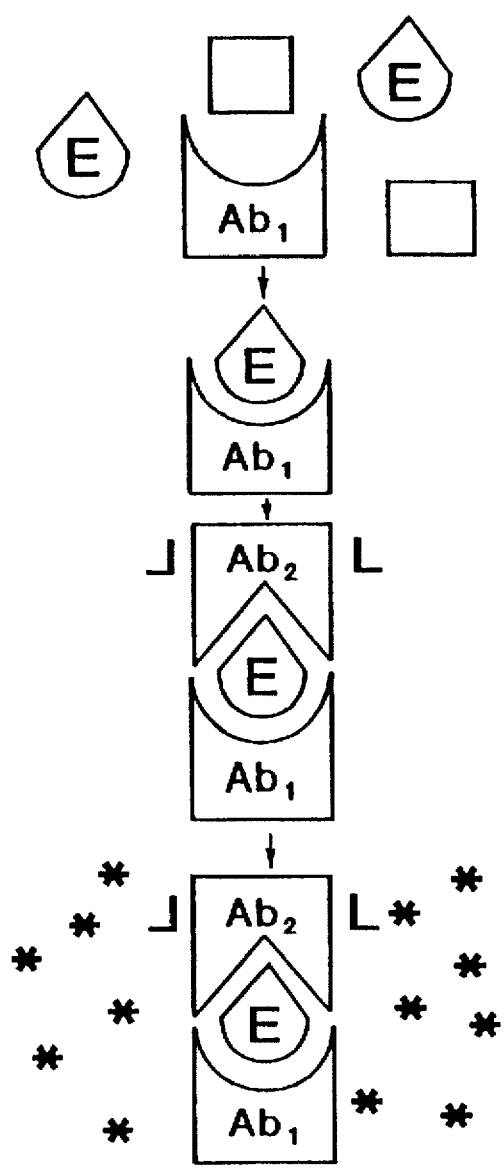
FIG. 1 is a schematic diagram illustrating the concept of the general assay method.

In describing the preferred embodiment of the invention which is illustrated in the drawings, specific terminology is resorted to for the sake of clarity. However, it is not intended that the invention be limited to the specific terms so selected and it is to be understood that each specific term includes all technical equivalents that operate in a similar manner to accomplish a similar purpose.

Although a preferred embodiment of the invention has been herein described, it is understood that various changes and modifications in the illustrated and described structure can be affected without departure from the basic principles that underlie the invention. Changes and modifications of this type are therefore deemed to be circumscribed by the spirit and scope of the invention, except as the same may be necessarily modified by the appended claims or reasonable equivalents thereof.

DETAILED DESCRIPTION OF THE INVENTION AND BEST MODE FOR CARRYING OUT THE PREFERRED EMBODIMENT

Referring to FIG. 1, there is shown a reaction scheme according to this invention for a rapid and sensitive two site immunoassay for allergens, especially airborne allergen enzymes. Antibody ($Ab_1$) has been insolubilized on the surface of polystyrene microwells through hydrophobic interaction. This solid-phase antibody ($Ab_1$) is used to bind an allergen such as enzyme (E) from a sample portion (solution) of allergen sample. A labeled antibody ($Ab_2$) is transferred to the solution and reacts to bind to the bound enzyme at a second site. The excess sample solution and labeled antibody are removed from the microwell by washing. A color developing reagent (chromogenic substrate) is transferred to the microwell reaction site. A labeling substance such as alkaline phosphatase that is conjugated to the labeled antibody reacts with a substrate such as the chromogenic substrate para-nitrophenyl phosphate, to form a yellow colored reaction product (*). The substrate-enzyme reaction is stopped and the color intensity is measured at 405 nm using a plate reader. The absorbance is proportional to the amount of allergen in the sample solution and is quantified by comparing it with the absorbance of known amounts of the allergen.

Materials

Subtilisin Carlsberg (EC 3.4.21.14, ALCALASE, 2.OT, NOVO Nordisk, Denmark), SAVINASE (EC 3.4.21.14, 4.OT, NOVO Nordisk, Denmark), and Subtilisin BPN' (EC 3.4.21.14, Sigma Chemical Company, St. Louis, Mo.) were obtained as a prill or powder.

Protein Assay. Protein content of antibodies and allergens was determined using a microwell plate adaptation of the Lowry method.[31] Reference standards of bovine serum albumin (BSA; Sigma Chemical Co., St. Louis, Mo.) in phosphate-buffered saline (PBS; 150 mM sodium chloride and 10 mM sodium phosphate, pH 7.2) were also prepared daily. The protein content of the reference BSA standards was determined using an extinction coefficient of 0.66 at 1 mg/mL and 280 nm.[32] The Lowry assay was performed in 13×100 mm glass tubes and then 200 µL of the assay solution was transferred to a microwell of an Immulon IV plate (Dynatech, Chantilly, Va.). The absorbance was determined using a Vmax plate reader and SOFTmax software for data analysis (Molecular Devices, Menlo Park, Calif.) interfaced to a computer and printer. Protein concentrations were determined from a linear regression plot of the standards.

Antibody Preparation. Antibodies to various allergen proteases were prepared in New Zealand white rabbits. Proteases were inhibited with 1 mM phenylmethylsulfonyl fluoride for 15 min at room temperature, dialyzed against 3×100 vol of Dulbecco's phosphate buffered saline (PBS), and then stored at −20°±5° C. at 5 mg/mL. The allergen solution was analyzed for protein concentration using the Lowry assay[33] and for remaining enzyme activity using a chromogenic substrate assay.[34] Five New Zealand white rabbits were immunized with 1 mg antigen/rabbit/injection mixed in Complete Freund's Adjuvant (DIFCO, Detroit, Mich.) for initial injections and incomplete Freund's Adjuvant for subsequent injections at subcutaneous perilymph node and intramuscular sites on days 0, 21, 42, and 63. Sera were collected from the animals on days-1, 31, 52, and 73 of the immunization schedule, heat inactivated at 56°±2° C. for 30 min, and then stored a −20°±5° C. The antisera titer were determined using an indirect enzyme-linked immunosorbent assay as described by Voller et al.[35]

Allergen specific antibodies was prepared by affinity chromatography. The allergen was coupled to 10 mL of CNBr-activated Sepharose 4B gel (Pharmacia Biotechnology, Piscataway, N.J.) and 50 mL of antiserum was applied to the immobilized enzyme. Unbound serum proteins were washed from the column with PBS and the bound antibodies were eluted from the enzyme-gel matrix using 0.87M acetic acid at pH 2.5 into a fraction collector with tubes containing 2M potassium phosphate, pH 8.0. The purified antibody was evaluated for activity using an indirect enzyme-linked immunosorbent assay[36] and for protein content by absorbance at 280 nm.

Labeled Substance (Antibody). A labeled substance (antibody-enzyme immunoconjugate) was prepared for the two-site immunoassay. Affinity-purified antibody (2.5 mg) was reacted with 0.85 mg sulfo-succinimidyl 4-(N-maleimidomethyl)cyclohexane-1-carboxylate, SMCC (Pierce Chemical Co., Rockford, Ill.) in 2.0 mL PBS at pH 7.0. Five milligrams of alkaline phosphatase (Biozyme Laboratories International Ltd., San Diego, Calif.) was activated with 0.5 mg iminothiolane (Pierce Chemical Co., Rockford, Ill.) in 2.0 mL 0.1M N-ethyl-morpholine hydrochloride buffer at pH 7.0. These reactions were performed separately and simultaneously for 1 hr at 30° C. The unreacted SMCC and iminothiolane was removed by size exclusion chromatography on a Sephadex G25 column (Pharmacia LKB Biotechnology, Piscataway, N.J.). The activated antibody and labeling agent (iminothiolane reacted enzyme) were used to form a labeled substance (antibody-enzyme immunoconjugate) by combining and reacting them for an additional 1 hr at 30° C. The resulting labeled substance (antibody-enzyme immunoconjugate) was analyzed for activity using an indirect enzyme-linked immunosorbent assay.[37]

Reaction Site (microwell) Antibody Insolubilization. Antibody-coated microwell plates (Immulon IV, Dynatech, Chantilly, Va.) were prepared by incubating 100μL of affinity-purified antibody at 2 μg/mL in 50 mM sodium bicarbonate buffer, pH 9.7 in each well (reaction site) at 2°–8° C. for 16–20 hrs. The use of purified antibody has the advantage of providing a greater number of reaction sites in each well that are specific for the target allergen. This provides faster reaction and greater assay sensitivity by increasing the number of specific binding sites while reducing assay contamination as a result of binding of nonspecific materials. The wells were then washed with 5×300 μL wash buffer (500 mM NaCl, 20 mM Tris, 0.02% BSA, 0.1% Tween 20, and 0.05% sodium azide at pH 8.0). The microwells were then treated with 300 μL of an overcoating solution (150 mM sodium chloride, 10 mM sodium phosphate, 1% BSA, and 0.1% sodium azide, pH 7.2) for 1 hour at room temperature and the excess solution was decanted. Overcoating has the advantage of protecting the bound antibody as well as blocking binding sites that are nonspecific for the target allergen. After drying the microwell plates at 4° C. overnight in a desiccated chamber, they were stored in sealed polyethylene bags with desiccant at 2° to 8° C.

Air Samples. Air samples from a detergent manufacturing site were collected for 120 min using a high volume air sample (26–30 cu ft/min) containing glass fiber filters (Whatman GF/C). These filters have an average pore diameter of 1.5 μm and a collection efficiency of ≧90% for particles ≧1.5 μm in diameter.

Sample Preparation Buffer. The sample preparation buffer maintains the pH in the range of 7–10. Preferably a Tris (tris(hydroxy-methyl) aminomethane) buffer is used at pH 8.2. Although it is possible to use other buffers, care must be exercised since some buffers such as a phosphate buffer have been found to be detrimental to the removal of sample allergen from the sample.

The ionic strength of the sample preparation buffer is typically in the range of 150–1000 mM with the use of 500 mM sodium chloride being preferred. Other ions such as other alkali halides, e.g., KCl and NaBr, may be used to obtain the desired ionic strength, but sodium chloride is preferred because of its ready availability, purity, and cost. The ionic strength of the sample buffer also serves to reduce nonspecific binding between the antibodies and sample materials that do not have specific determinants for the antibodies.

In addition to the ionic strength of the buffer, bovine serum albumin (BSA; 0.01 to 1 wt %) and Tween 20 (0.01 to 1 wt %) are also used to reduce further nonspecific binding. BSA is also used in high concentration (>1000 fold excess) along with calcium chloride (0.1 to 10 mM) to stabilize the enzyme against auto- and antibody degradation by providing an alternative substrate for the enzyme. Although other reagents such as those that deactivate an enzyme may be used for this purpose, it has been found the combination of BSA and calcium chloride are stable and therefore require less frequent preparation and can be used for most allergens, especially enzyme allergens. Other reagents such as phenyl boronic acid, phenylmethylsulfonyl fluoride, iodoacetate-glycerol solutions tend to be limited to specific classes of allergens. In addition, some reagents such as phenylmethylsulfonyl fluoride undergo decomposition requiring preparation of fresh solutions immediately prior to use.

An oxidizing agent neutralizer such as sodium thiosulfate (1.0 to 100 mM) is used as a reducing agent to neutralize oxidizing agents in the sample (e.g., bleach). Although other water-stable, mild reducing agents may be used, care must taken in their use so as to avoid interference with the protein as a result of denaturation especially as a result of disulfide linkage disruption, especially for the antibody molecule.

An antimicrobial agent such as sodium azide is used to prevent microbial growth in the sample and typically used in concentrations of 0.0001 to 1 wt %. Other common antimicrobial agents such as sodium benzoate, cycloheximide, merthiolate or other antimicrobial agents may be used but care must be taken to avoid interactions with the target allergen or various other reagents used in the assay.

Although a wide variety of reagent substitutions will be apparent to those skilled in the art and may be prepared according to the above guidelines, a typical and preferred sample preparation buffer useful for a broad scope of allergens both for target allergen elution from the sample and subsequent stabilization of the eluted allergen consists of 500 mM NaCl, 20 mM Tris, 0.1 wt % BSA, 20 mM sodium thiosulfate, 1 mM calcium chloride, 0.1 wt % Tween 20, and 0.1 wt % sodium azide at pH 8.2.

Sample Preparation

The glass fiber air filters were removed from the air sampler and placed in a 50 mL plastic conical centrifuge tubes. Twenty milliliters of sample preparation buffer were added to the air sample filters in the plastic tubes. The tubes were rotated at about 25–30 revolutions per minute for thirty minutes at room temperature to elute the target allergen which is decanted as the sample portion.

For the purposes of this invention, room temperature is defined as 21°±1° C. However, for this particular step, temperature control is not critical, it being realized that considerably lower temperatures will require a longer time for sample portion preparation while higher temperatures will require a corresponding shorter period.

Purified allergen was used to prepare standards or controls by diluting in sample preparation buffer. After preparation, all samples, standards and controls were maintained at 0°–10° C. and preferably at 2°–8° C. and most preferably at 5°±1° C. prior to use in the assay.

The sample preparation buffer elutes a sample portion (target allergen) from the sample and simultaneously stabilizes the target allergen. This technique is not only rapid but has been found to be effective in separating interfering components of the sample such as detergent surfactants and dust from the sample.

Immunoassay

To a previously prepared microwell reaction site with insolubilized antibody, 50 µL of cooled assay buffer (500 mM NaCl, 20 mM Tris, 0.15% BSA, 0.15% Tween 20, and 0.1% sodium azide at pH 8.2) was added to each well prior to heating and then 100 µL of the standard, control or sample portion was added. After a 15 min incubation at 37° C., 50 µL of the labeled substance antibody (alkaline phosphatase-antibody immunoconjugate) in assay buffer was added to each microwell. The plate was incubated at 37° C. for 135 minutes and then washed 5×300 µL with wash buffer containing 500 mM NaCl, 20 mM Tris, 0.02% BSA, 0.1% Tween 20, and 0.05% sodium azide, pH 8.0 to remove unbound material from the reaction site. Next, 100 µL of wash buffer and a chromogenic substrate, 2 mM paranitrophenyl phosphate in 1.0M diethanolamine buffer at pH 10.0 (Kirkegaard and Perry Laboratories, Gaithersburg, Md.) were added to each microwell and the plates were incubated at 37° C. for 30 min. This enzymatic reaction was stopped by adding 100 µL of 7.5% ethylenediaminetetraacetic acid (EDTA) containing 1M potassium phosphate and 0.02% sodium azide at pH 10.0. The absorbance of the colored reaction product at 405 nm was measured using a BioTek plate reader and KinetiCalc software, version 1.11(BioTek, Winooski, Vt.) interfaced to a computer and printer. The absorbance values were compared with absorbance values of specific amounts of allergen standards substituted for the sample and determined by the same method.

Desiccator

Figure 6:
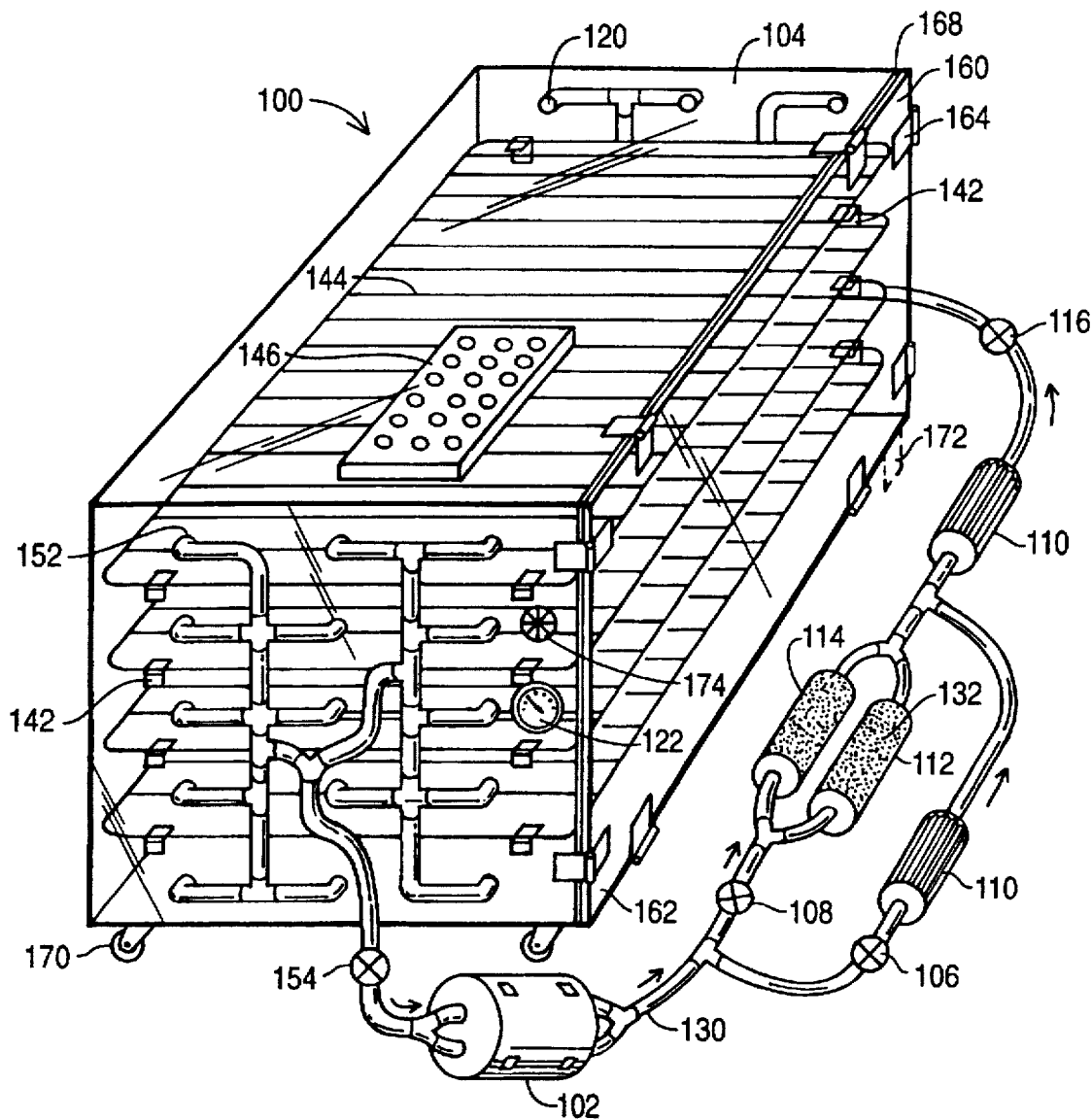
FIG. 6 is a perspective view of the desiccator used in this invention.

A perspective view of the desiccator 100 used in this invention is shown in FIG. 6. A dual head vacuum pump 102 is used to recirculate air through the desiccator chamber 104 at a flow rate of about 18 liters per minute in a closed loop arrangement through flexible plastic tubing 130. Air flow direction is represented by the arrows. The total air inlet flow is divided and controlled by 1) the air bypass valve 106 and drying agent control valve 108 which have been calibrated for maximum flow rate and drying efficiency using a 0–40 liter per minute in-line mass flow meter. The air is dried by circulating it through the drying agent, e.g., $CaSO_4$, 132 located in drying tubes 112 and 114. A 0.2 µm particle filter 110 is used downstream of the drying agent columns 112 and 114 to purify the recirculating air flow before entering changer 104.

Air inlet valve 116 controls the air flow entering chamber 104 at 15 separate ports 120 consisting of three ports at each of five shelf levels in chamber 104. Inlet valve 116 can be adjusted to decrease the air flow entering the chamber thereby creating a negative pressure monitored by the use of a 0–2.0" $H_2O$ magnehelic gauge 122 that measures the differential pressure between the outside environment and the drying chamber. An inlet 174 is provided for a temperature and humidity probe. Circulating air leaves chamber 104 through exhaust ports 152, passes through valve 154 and enters pump 102.

Wire racks 144 reset on support members 142 located at each end of chamber 104 and are used to support microwell plates 146 during the drying process. The chamber 104 is accessed through a port 160 (open side of chamber 104) by removing chamber side 162. Chamber side 162 is held in place by fasteners 164 which also seal side 162 to the remaining walls of the chamber by means of a resilient seal 168. The rectangular shape of chamber 104 facilitates stacking. Rollers 170 may be added to facilitate movement while legs 172 (shown in phantom) are used to keep the desiccator bottom off of the floor while still allowing stacking of the desiccator.

Immunoassay Equipment

Figure 2:
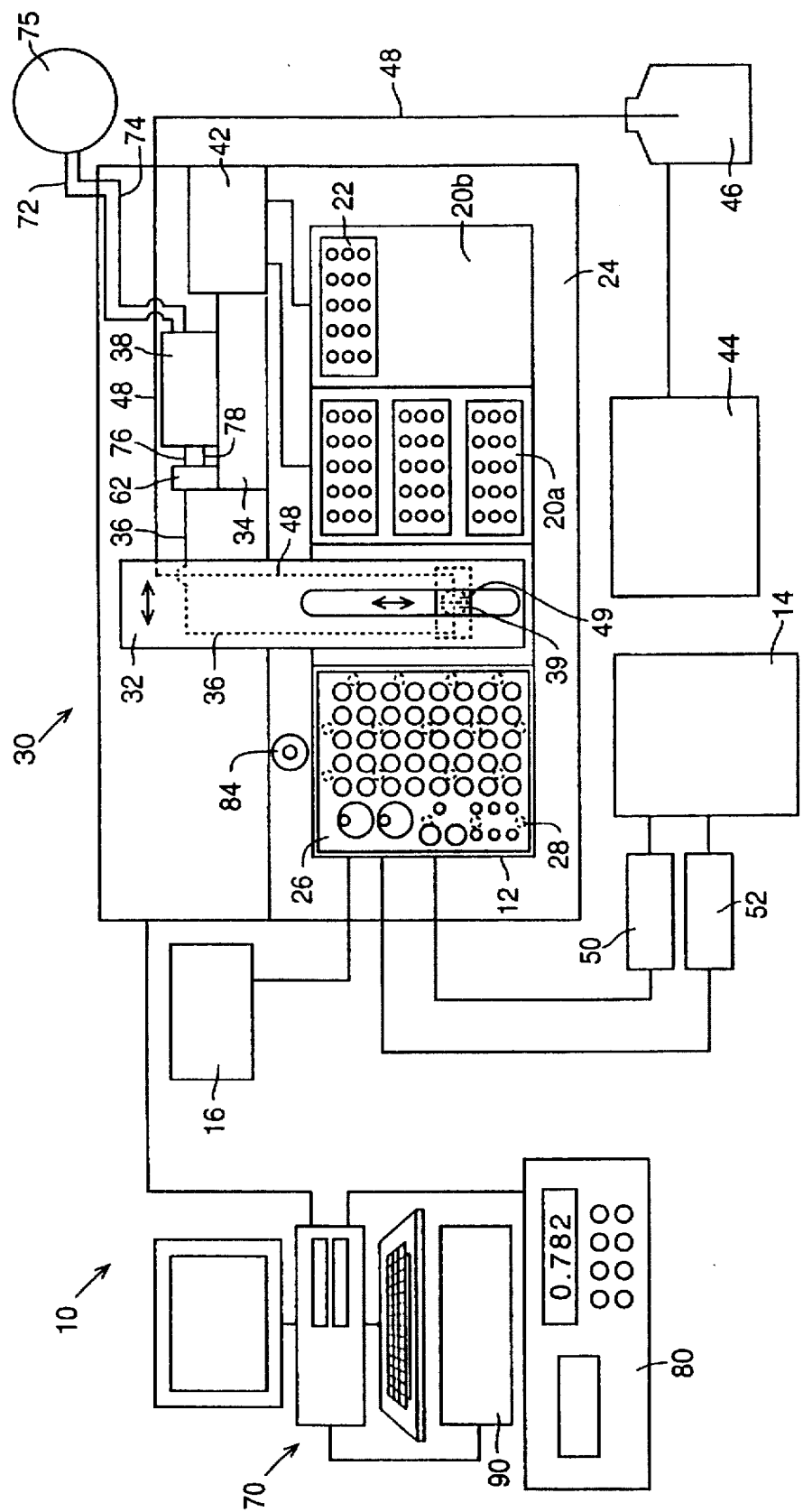
FIG. 2 is a schematic diagram showing the components of an automated allergen immunoassay system.

A schematic diagram of the automated allergen immunoassay system is shown in FIG. 2. The immunoassay system 10 consists of a liquid handling system 30 such as a modified Tecan RSP Model 5051 (Tecan U.S., Hillsboro, N.C.), an IBM compatible computer 70, dot matrix printer 90 and plate reader 80. The liquid handling system 30 has a deck 24, liquid transfer arm 32 mounted to deck 24, solution pumps 34 for dispensing liquids, a vacuum pump 44 for withdrawing liquids through vacuum line 48 and probe tip 49, and waste receptacle 46. A wash buffer supply 75 is fed via lines 72 or 74 into input/output valves 38 for metering via pumps 34. On leaving input/output valves 38, liquid passes through line 76 or 78 to feed valve 62 and then through line 36 to probe tip 39. Probe tip 39 is washed in wash well 84.

The Tecan system was modified by equipping it with a water bath reagent rack 12 that was connected to a cooler 14 (Isotemp Refrigerated Circulator, Model 9100, Fisher Scientific, Pittsburg, Pa.). A type-T thermocouple 16 with digital display (DP460, Omega Engineering, Stamford, Conn.) was used to monitor the water bath reagent rack temperature. The water bath reagent rack 12 was used to hold the reagents and samples in the appropriate tubes or bottles at a defined location on the deck 24 of the liquid handling system 30 and to maintain the temperature at 5°±2° C., preferably at 5°±1° C. and most preferably at 5°±0.1° C. Two heating blocks 20a and 20b with mounting pads for 3 microwell plates 22 each and thermocouples 42 with digital temperature displays were used to maintain the temperature of each microwell plate at 37°±2° C. and preferably at 37°±1° C. In using the heating blocks during the assay, it was found advantageous to add assay buffer to the wells of the microwell plates prior to placing them on the heating blocks and adding sample. A computer program for the two-site immunoassay was developed for operating the immunoassay system using RSP Integrator Software, version 7.30 (Tecan U.S., Hillsboro, N.C.).

The immunoassay system 10 performed many of the steps of the allergen immunoassay (Table I). The transfer of given amounts of sample, labeling antibody, chromogenic substrate, washing and stop solutions; reaction (incubation) times; and plate absorbance and data analysis were performed automatically. Only sample and reagent preparation and transfer of the microwell plate to the reader were performed manually. In addition, as many as 160 samples plus standards and controls were analyzed for 4 different enzymes in duplicate in one run. The total assay time was approximately 5 hrs and 50 mins with only 90 mins technician attended time.

TABLE I

Enzyme Immunoassay Steps Automated by Robotic System

| STEP | MANUAL | AUTOMATED |
|---|---|---|
| Sample Collection | + | |
| Sample Preparation | + | |
| Immunoassay | | |
| setup equipment | | + |

TABLE I-continued

Enzyme Immunoassay Steps Automated by Robotic System.

| STEP | MANUAL | AUTOMATED |
|---|---|---|
| prepare reagents and samples | + | |
| two-site immunoassay | | |
| add assay buffer | | + |
| add samples to plates | | + |
| incubate for 15 min | | + |
| add labeling antibody | | + |
| time incubation for 135 min | | + |
| wash wells 5x with buffer | | + |
| add chromogenic substrate | | + |
| time incubation for 30 min | | + |
| add stop solution | | + |
| generate database | | + |
| wash probe tip | | + |
| Data Analysis | | |
| transfer plate to reader | + | |
| read absorbance | | + |
| data analysis | | + |

The liquid handling system 30 required the design and construction of two temperature controlling systems. A water bath reagent rack 12 was used to maintain assay reagents and samples at a low temperature of preferably 5°±0.1° C. to prevent or reduce reagent activity changes during the allergen immunoassay. It was designed to position containers for all allergen immunoassay reagents and samples at specified locations on the liquid handling system deck 24. Cooling rack 12 was constructed of 3/16" polypropylene with 1" walls insulated with polyurethane foam. The bottom portion of the water bath rack 12 contained a baffle 26 to maintain even water temperature distribution by allowing cooled liquid to enter the reagent rack 12 below baffle 26 and circulate upward through apertures 28 in baffle 26. A thermocouple 16 (type T) with digital display was installed with the water bath reagent rack 12 for convenient temperature monitoring in the water bath reagent rack 12. A recirculating temperature controller 14 containing 5% ethylene glycol/water (volume/volume) solution and flow control valves 50 and 52 were used to maintain the temperature at 5°±0.1° C.

Heating blocks 20a and 20b were used to adjust the temperature of the microwell plates to a constant, elevated temperature for the allergen immunoassay. The heating blocks were Peltier type and were constructed of anodized aluminum block with a conductive heating coil, thermocouple 42 with microprocessor controlled rheostat and digital temperature display. Each heating block held three microwell plates 22 and had alignment pins to position the plates over the heating area. The temperature distribution of the microwell plates on the heating blocks was determined using 200 µL of assay buffer in four corners and one middle microwell of the plates at each position. The mean temperature for the three microwell plates was 39.0°±0.9° C. for block 1 and 38.3°±0.3° C. for block 2.

RSP Integrator Software (version 7.30) was used to develop a program for performing the allergen immunoassay liquid handling steps for four different enzymes by the liquid handling system 10. This software provided control for liquid transfer arm 32 position, liquid transfer and handling, vacuum line valve control for liquid withdrawal, vacuum line washing and drying, dispensing tip washing, and timing of all operations. The liquid handling system performed the sequence of operations outlined under the heading "two-site immunoassay" in Table I.

Figure 7A:
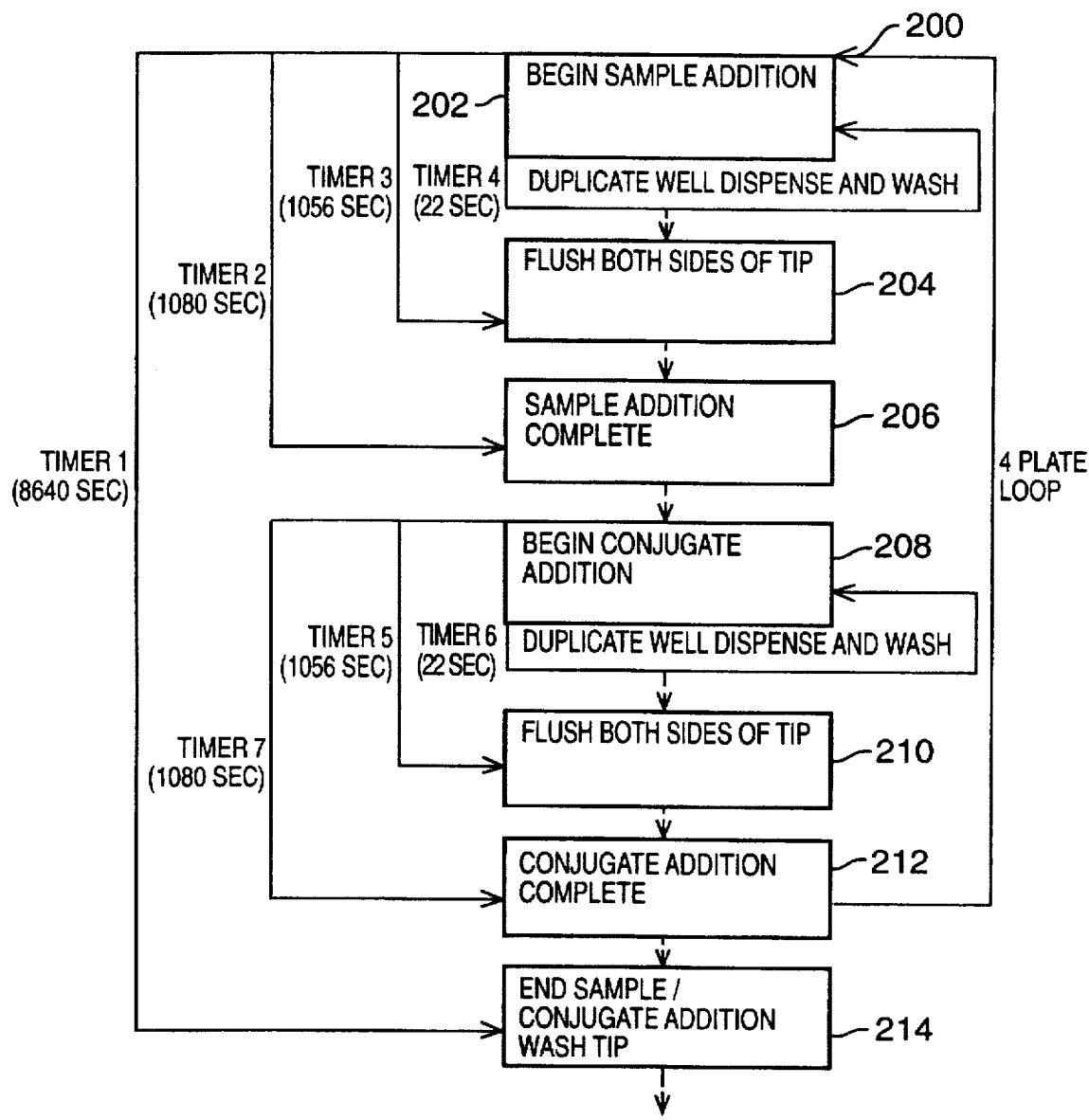
FIG. 7 consists of three parts labeled FIG. 7a, FIG. 7b, and FIG. 7c and shows a flow diagram for the control software that uses timers to monitor the progress of the assay and add various reagents.
Figure 7B:
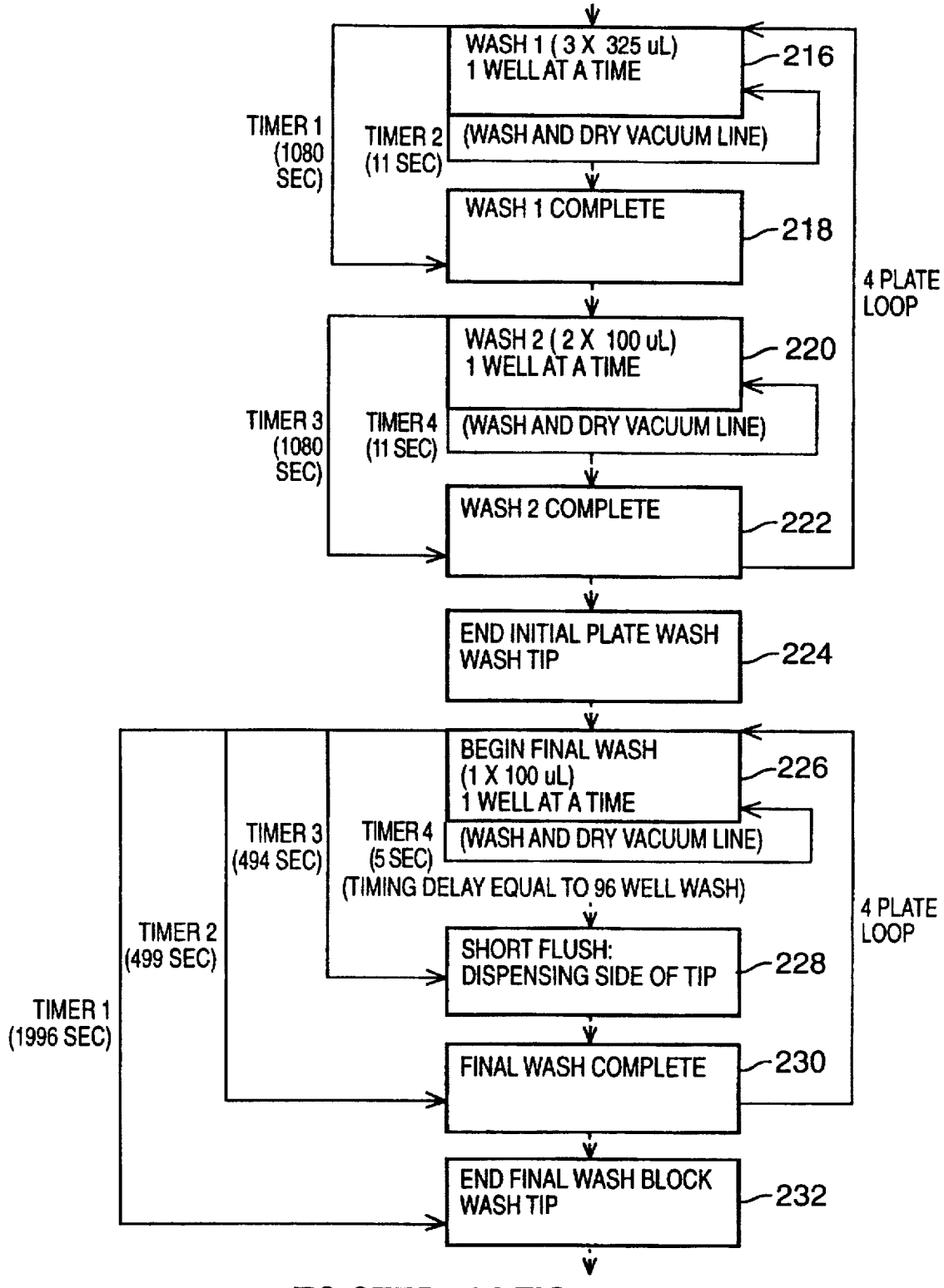
Figure 7C:
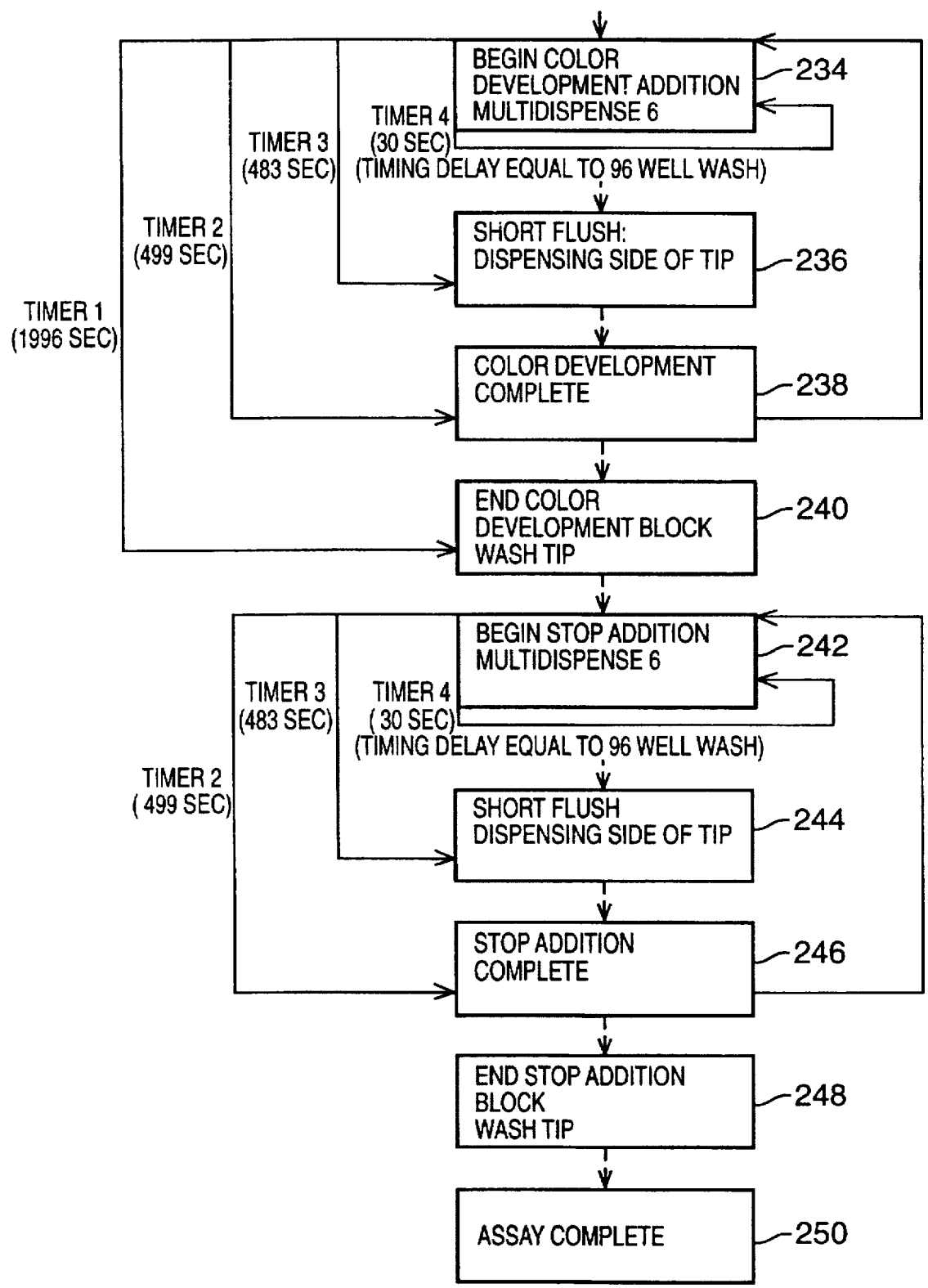

FIG. 7a–7c gives a flow diagram for the control software timing sequence. The operation begins with step 200, the addition of sample to each well of a plate. The sample is dispensed to duplicate wells and the probe tip is washed. After all wells of a plate are completed, both the vacuum and liquid sides of the probe tip are flushed in step 204. This completes the sample addition for the first plate, 206.

Next the labeled substance (conjugate) is added in step 208 to duplicate wells followed by a probe tip wash. After completion of all wells on the plate, both sides of the probe are flushed 210 to complete the labeled substance addition 212 for one plate. The cycle returns to step 200 for the next three plates until all plates are completed after which the probe tip is washed in step 214. Starting at step 216 of FIG. 7b, each of the wells is washed 5 times. First each well on a plate is washed three times 216 after which the vacuum line is washed and dried completing first wash 218. Next each well of a plate is washed two more times 220 followed by a wash and dry of the vacuum line to complete the second wash 222. The process cycles through steps 216 through 222 until all of the plates are completed after which the probe tip is washed 224.

Next the final wash is begun at 226 where each well is washed once, one well at a time, after which the vacuum line is washed and dried. Next the dispensing side of the tip receives a short wash 228 followed by a final complete wash in step 230 after which the process cycles through steps 226 through 230 to complete the remaining plates. The final wash loop is completed with a washing of the probe tip in step 232.

Proceeding to FIG. 7c, the substrate is added six wells at a time in step 234 after which the dispensing side of the tip is flushed 236 and the color development cycle for the first plate is complete 238 after which the remaining three plates are cycled through steps 234 through 238 ending at step 240 with a probe tip wash 240.

Proceeding to step 242, the reaction stop reagent is added to six wells at a time after which there is a short flush of the dispensing side of the probe tip in step 244 after which the stop addition cycle is complete for the first plate 246. The cycle repeats until all plates are finished after which the tip is washed in step 248 to conclude the assay in step 250.

As was noted previously, it is desirable to add assay buffer to the microwells prior to heating and the addition of sample (step 200). Such addition can be done manually especially using a multichannel micropipette or an additional program loop may be provided prior to step 200 for such addition. Preferably an additional site is provided on the equipment deck for location of the microwell plates for this step and then the plates are transferred to the heating blocks.

During the development of this program, several software and hardware factors were evaluated to obtain high pipetting volume precision and accuracy. Liquid dispensing arm speed, pump rates, air gap (the amount of air between liquid withdrawn into the probe and the probe tip necessary to avoid evaporation of sample and reagents during reagent transfer operations), probe priming volume (the initial volume of liquid entering the probe and wetting the probe inner surface), probe washing, and condition of probe tip and liquid lines were found to be critical aspects for this system. Although these parameters are functions of the specific liquid handling system and are typically detailed to the user by the manufacturer of the system, it is essential that they be evaluated and maximized to obtain optimal assay values. During the development of the liquid handling software, the two-site allergen immunoassay was performed to confirm assay timing as well as precision. During these studies, the program was optimized by minimizing or eliminating those parameters that impacted each individual assay step.

The following factors were found to have considerable impact on assay precision:

1. Timing. During initial trials, it was found that reacting (incubation)times required tight control. Otherwise an increase in absorbance from left to right and from the first to last position on the microwell plate was noted. As a result, all reacting (incubating) steps are controlled to within ±1 second.
2. Pump Speed. If solution is aspirated or dispensed at too slow a rate, the assay time is increased unnecessarily. On the other hand if these rates are too fast, the coefficient of variation and volume accuracy become unacceptable due to rapid dispensing and bubbling of reagents resulting in missed wells.
3. Air Gap. A sufficient air gap between the end of the probe tip and the liquid in the probe must be established to prevent liquid evaporation while the robotic arm transfers liquid from source to destination.
4. Priming volume. The priming volume is the initial volume that enters the probe and wets the probe's inner surface.
5. Probe Washing. Washing the probe tip after each reagent and sample handling is essential. The probe was typically washed 5 times with 1 mL of wash buffer after each change in liquid.
6. Hardware. The condition of the probe tip and system tubing can also affect assay precision and accuracy. There is a tendency for the Teflon coating on the probe tip to flake away. This problem can be avoided by washing the probe at the end of each run and replacing the probe when evidence of Teflon deterioration appears. System tubing should also be inspected periodically and replaced every six months. Table II indicates those assay steps affected by volume variation, incubation time and probe washing.

TABLE II

| Factors Effecting Automated Enzyme Immunoassay | | | |
|---|---|---|---|
| Assay step | Volume | Incubation Time | Probe Wash |
| sample | + | + | + |
| labeled substance | + | + | – |
| microwell wash | – | – | – |
| substrate | + | + | – |
| stop solution | – | – | – |

Pipetting precision and accuracy studies were performed using a solution of 0.0014% DNP-glycine (dinitrophenyl-glycine) in assay buffer. To a microwell plate, 60 replicates each of 50 µL or 100 µL DNP-glycine solution was dispensed using the liquid handling system. As a reference, a 12-channel manual pipetter was calibrated gravimetrically and was used to deliver 12 replicates of these volumes. For the liquid handling system, the mean absorbance values were 0.282±0.003 for 100 µL and 0.135±0.004 for 50 µL resulting in a precision with a 1.0% coefficient of variation (CV) and 3.1% CV, respectively. The calibrated manual pipetter produced mean absorbance values of 0.285±0.002 at 100 µL and 0.133±0.005 at 50 µL resulting in a 1.0% and 1.5% difference in pipetting volume accuracy.

In using four microwell plates, position 1, 2, and 3 of heating block 1 and position 1 on heating block 2 were used (FIG. 2). To test the uniformity of volume dispensing and position to position consistency of the timing schedule for the various assay steps, 0.6 ng/mL of Subtilisin Carlsberg, Subtilisin BPN', SAVINASE, AND CELLULASE was used in the two-site immunoassay. There were no significant difference in the absorbance values for the various plate positions in each allergen immunoassay with the percent coefficient of variation (CV) ranging from 2.5–4.2% (Table III).

TABLE III

| | Comparison of Microwell Plate Position. | | | | |
|---|---|---|---|---|---|
| Enzyme | Plate Position | | | | |
| Immunoassay | 1 | 2 | 3 | 4 | |
| Subtilisin | 0.154[a] | 0.146 | 0.150 | 0.141 | 0.148[c] |
| Carlsberg | (5.3%)[b] | (3.7%) | (3.5%) | (3.8%) | (4.1%) |
| Subtilisin | 0.123 | 0.118 | 0.121 | 0.117 | 0.120 |
| BPN' | (3.7%) | (4.8%) | (5.4%) | (5.4%) | (4.8%) |
| SAVINASE | 0.163 | 0.153 | 0.158 | 0.151 | 0.156 |
| | (3.4%) | (5.2%) | (3.7%) | (3.6%) | (4.0%) |
| CELLULASE | 0.131 | 0.138 | 0.140 | 0.128 | 0.134 |
| | (2.8%) | (2.9%) | (1.9%) | (2.9%) | (2.6%) |

[a]Mean absorbance at 405 nm of 60 replicates for 0.6 ng enzyme/mL.
[b]Percent coefficient of variation.
[c]Grand mean and percent coefficient of variation of four plate positions.

A timing chart for the optimized liquid handling system allergen immunoassay is shown in FIG. 3 describing the timing sequence for each step. A total assay time of 5.5 hours was needed to dispense reagents for 40 tests and 4 enzymes resulting in an average sample throughput time of 2 minutes.

Allergen Immunoassay Characteristics

Figure 4A:
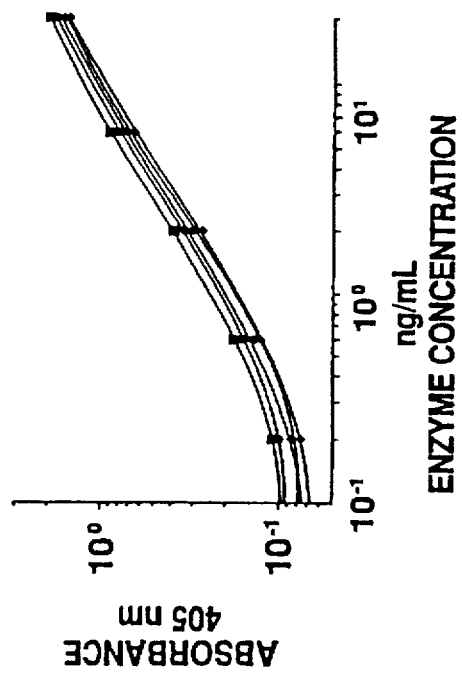
FIGS. 4a–4d show the optimization curves used in defining enzyme detections limits. Absorbance values (405 nm) for the colored product at various levels of labeled antibody dilutions (1:100 (■), 1:200 (●), 1:400 (▲), 1:600 (▼), 1:800 (♦), and 1:1000 (+) for Subtilisin Carlsberg (FIG. 4a), SAVINASE (FIG. 4c), and CELLULASE (FIG. 4d) and 1:200 (■), 1:100 (●), 1:1200 (▲), 1:1400 (▼), 1:1600 (♦), and 1:1800 (+) for Subtilisin BPN' (FIG. 4b). Absorbance values are means of duplicates. The curves are third order polynomials.
Figure 4B:
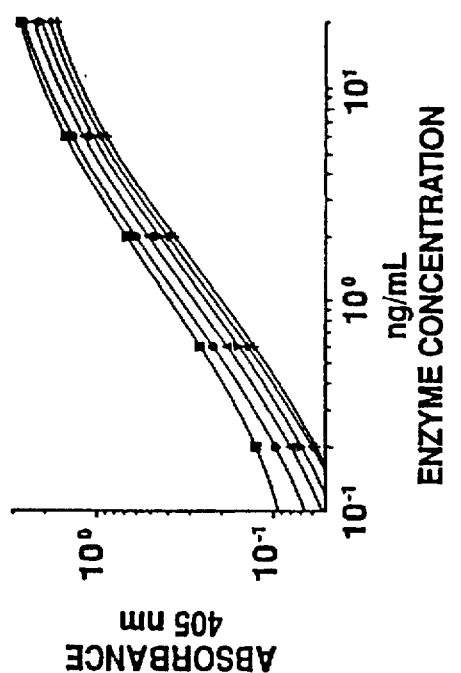
Figure 4C:
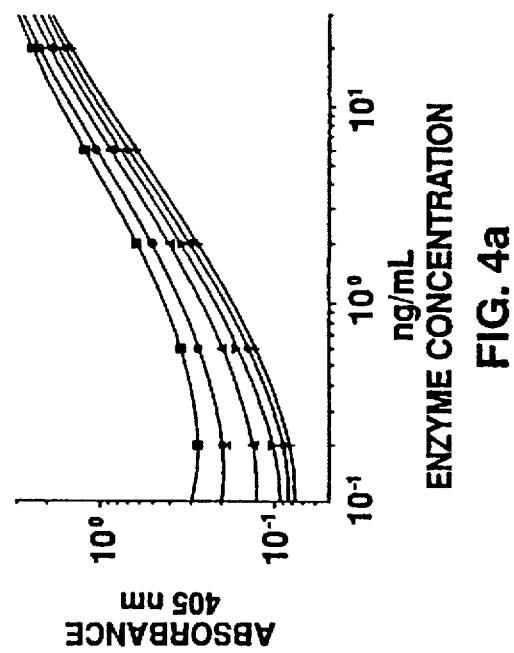
Figure 4D:
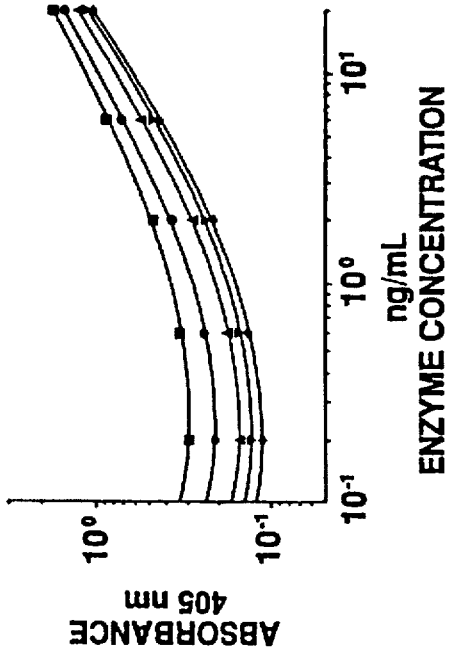

Labeling Antibody Optimization. The immunoassay was optimized by varying the labeling antibody concentration to achieve a 0.2 ng/mL detection limit. Enzyme standards of 0, 0.2, 0.6, 2, 6, and 20 ng/mL were reacted with labeling antibody at dilutions ranging from 1:100 to 1:1,800. A detection limit of 0.2 ng/mL was achieved using a dilution of 1:600 for Subtilisin Carlsberg (FIG. 4a), 1:1,400 for Subtilisin BPN' (FIG. 4b), 1:100 for SAVINASE (FIG. 4c), and 1:800 for CELLULASE (FIG. 4d). The response range of the standard curve was 0.2–20 ng/mL for each enzyme.

Assay Precision. Studies were performed to determine the intra- and inter-assay reproducibility of the automated allergen immunoassay. For the inter-assay reproducibility study, 28 replicates of 0.6 ng/mL and 6 ng/mL enzyme was performed for each optimized allergen immunoassay. The percent coefficient of variation values ranged from 3.2–4.3% at 0.6 ng/mL and 1.8–2.7% at 6 ng/mL (Table IV).

TABLE IV

| Intraassay Reproducibility | | |
|---|---|---|
| Enzyme | Enzyme Concentration | |
| Immunoassay | 0.6 ng/mL | 6 ng/mL |
| Subtilisin Carlsberg | 0.172 (4.3%)[a] | 0.942 (1.8%) |
| Subtilisin BPN' | 0.153 (4.0%) | 0.711 (2.5%) |
| SAVINASE | 0.166 (3.4%) | 0.907 (2.7%) |
| CELLULASE | 0.142 (3.2%) | 0.861 (2.7%) |

[a]Mean absorbance at 405 nm and percent coefficient of variation for 28 replicates.

For the interassay reproducibility study, the optimized SAVINASE allergen immunoassay was performed in twenty replicates on three consecutive days. The mean absorbance values for each replicate were 0.130±0.007 (5.4% CV), 0.128±0.006 (4.7% CV), and 0.116±0.006 (5.0% CV) with a grand mean and standard deviation of 0.125±0.008 (6.4% CV) at 0.6 ng/mL an 0.732±0.031 (4.2% CV), 0.709±0.043 (6.0% CV), and 0.679±0.016 (2.3% CV) with a grand mean and standard deviation of 0.707±0.027 (3.8%) at 6 ng/mL.

Assay Accuracy. The accuracy of the allergen immunoassays was determined by recovery studies. In a 50 mL tube, 20 mL of 0 ng enzyme/mL or 2 ng enzyme/mL sample preparation buffer were added to air sample filters from The Proctor and Gamble Company. The tubes were rotated for 30 min at room temperature and the supernatants were collected. The supernatants from tubes containing an air filter with sample preparation buffer, an air filter with enzyme solution, untreated sample preparation buffer, or 2 ng enzyme/mL solution were analyzed in the allergen immunoassay. The percent recovery was calculated by dividing the absorbance value for the air filter treated enzyme solutions after correction for endogenous enzyme by the corresponding corrected absorbance value for the untreated enzyme solution. The assay accuracy was generally 100±2%. Percent recoveries for duplicate air samples were 100% for Subtilisin Carlsberg, 100% for Subtilisin BPN', 99% for SAVINASE, and 88% for CELLULASE. The recovery for the CELLULASE allergen immunoassay was lower than the other allergen immunoassays because one of the replicates was low (74%) but the other (101%) was comparable to the other enzymes.

Figure 5:
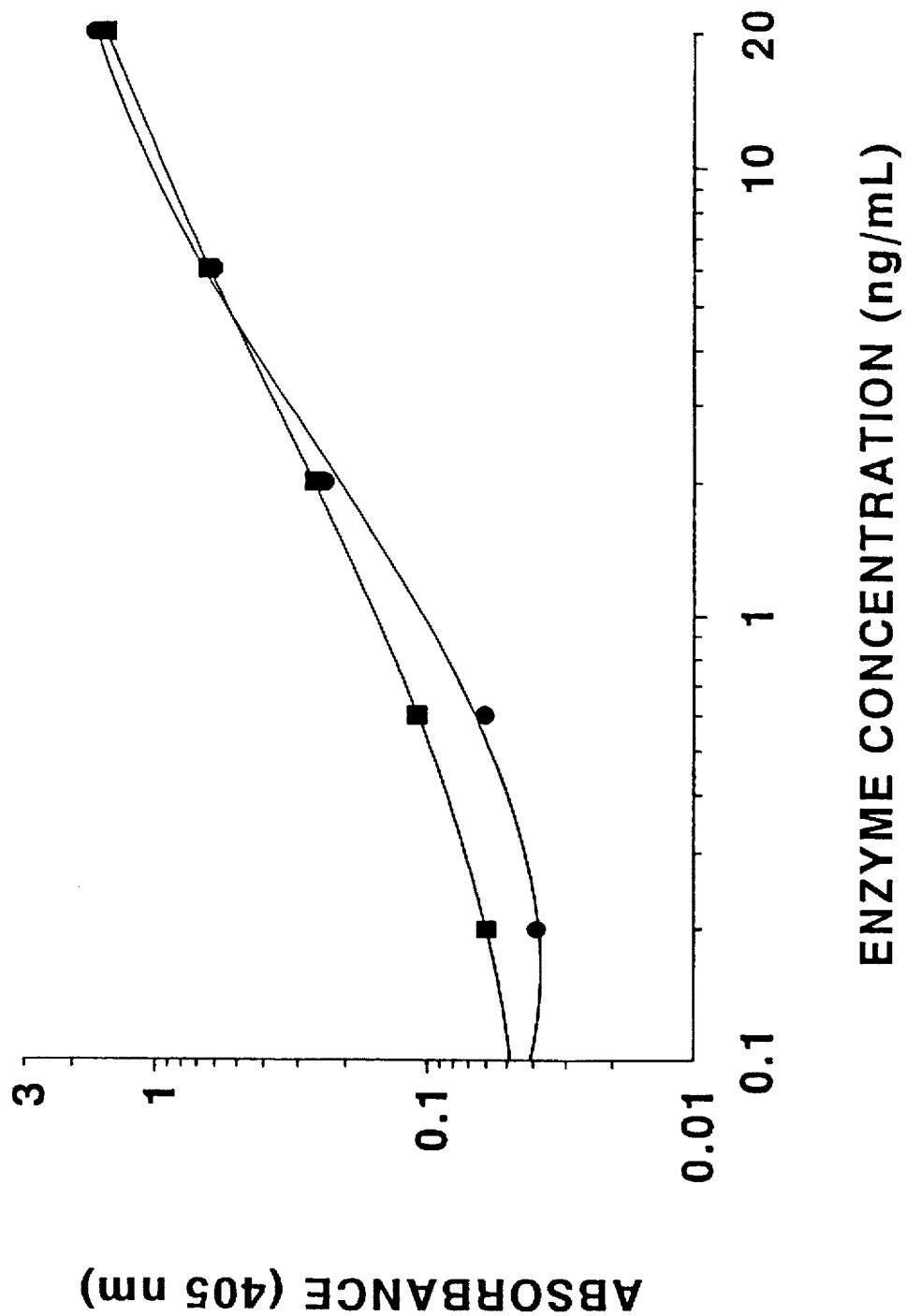
FIG. 5 gives the curves for a comparison of automated and manual allergen immunoassays. The allergen immunoassay for Subtilisin BPN' was performed by an automated (■) and a manual (●) method. The absorbance values are means of duplicates and the error bars indicated the standard deviation. The curves are third order polynomials.

Comparison of Manual and Automated Allergen Immunoassays. The automated immunoassay method was compared to a manual procedure for various assay characteristics including detection limit, response range, and precision. Subtilisin BPN' allergen immunoassay was used for this evaluation. For the manual method, all steps were performed the same as the automated method except the color development reagent was used at a 2-fold higher concentration. The mean absorbance values for the automated method were equivalent to the manual method (FIG. 5). However, if the color development reagent had been used at the same concentration, the values would have been approximately 2-fold lower than the automated allergen immunoassay. In part, this difference may be attributed to the continuous elevated incubation temperature for microwell plates in the automated method while for the manual method the microwell plates were removed from the incubator for each reagent addition and wash step resulting in intermittent cooling.

While there has been described what are at present considered to be the preferred embodiments of this invention, it will be obvious to those skilled in the art that various changes and modifications may be made therein without departing from the invention, and it is, therefore, intended to cover all such changes and modifications as fall within the true spirit and scope of the invention.

1. Swanson, M. C., Boiano, J. M., Balson, S. K., Grauvogel, L. W., and Reed C. E. "Immunochemical Quantification and Particle Size Distribution of Airborne Papain in a Meat Portioning Facility." *American Industrial Hygiene Association Journal*, vol. 53, no. 1 (1992), pp. 1–5.
2. Wells, J. D., Allan, R. E., Novey, H. S., Bulver, B. D. "Detection of Airborne Industrial Papain by a Radioimmunoassay" *American Industrial Hygiene Association Journal*, vol. 42, April (1981), pp. 321–322.
3. Dambmann, C., Holm, P., Jensen, V. and Nielsen, M. H. "How Enzymes Got Into Detergents." *Developments in Industrial Microbiology*, vol. 12, (1971), pp. 11–23.
4. Godfrey, T., "Comparison of Key Characteristics of Industrial Enzymes by Type and Source" in: Godfrey, *Industrial Enzymology* (England, MacMillan Ltd., 1983), pp. 466–502.
5. Dambmann, C. and Aunstrup, K. "The Variety of Serine Proteases and Their Industrial Significance" in: Turk et al., *Proteases and Their Inhibitors* (New York, Permagon Press, 1981), pp. 231–244.
6. Wells, op. cit.
7. Swanson, op. cit.
8. Flindt, M. H. L., "Pulmonary Disease Due to Inhalation of Derivatives of Bacillus subtilis Containing Proteolytic Enzyme" *The Lancet*, (1969), pp. 1177–1181.
9. Pepys, J., Hargreave, F. E., Longbottom, J. L., and Faux, J., "Allergic Reactions of the Lungs to Enzymes of Bacillus subtilis" *The Lancet* (1969), pp. 1181–1184.
10. Gilson, J. C., Juniper, C. P., Martin, R. B. and Weill, H., "Biological Effects of Proteolytic Enzyme Detergents" *Thorax*, vol. 31, (1976), pp. 621–631.
11. Data Index 5 "Current Industrial Enzyme Assays and Unit Definitions" in: Godfrey and Reichelt, *Industrial Enzymology* (England, MacMillan Ltd., 1983), pp. 553–557.
12. American Conference of Governmental Industrial Hygienists (ACGIH). *Documentation of Threshold Limit Values*. Fourth edition, Cincinnati, Ohio, (1980) pp. 374–375.
13. Data Index 5, op. cit.
14. Dunn, E. and Brotherton, R., "The Use of N,N'-Dimethylcasein in the Determination of Proteolytic Enzymes in Washing Products and Airborne Dust Samples." *Analyst vol.* 96, (1971), pp. 159–163.
15. Chien, P. T., "The Development of a Fluorometric Method for the Assay of Subtilisins" *American Industrial Hygiene Association Journal*, vol. 39, October (1979) pp. 808–816.
16. Fulwiler, R. D., Abbott, J. C., and Darcy, F. J., "Evaluation of Detergent Enzymes in Air" *American Industrial Hygiene Association Journal*, April (1972) pp. 231–236.
17. Hendricks, M. H., "Measurement of Enzyme Laundry Product Dust Levels and Characteristics in Consumer Use" *Journal of the American Oil Chemists' Society*, Jun. (1970) pp. 207–211.
18. Paixao, L. M., Babulak, W. W., Barkin, S. M., Shumway, D. K. and Friedman, S. D., "Automated Bioassay of Proteolytic Enzymes in Detergents" *Journal of the American Oil Chemists' Society*, October (1969) pp. 511–514.
19. Rothgeb, T. M., Goodlander, B. D., Garrison, P. H. and Smith, L. A. "The Raw Material, Finished Products, and Dust Pad Analysis of Detergent Proteases Using a Small Synthetic Substrate" *Journal American Oil Chemists' Society*, vol. 65, (1988), pp. 806–810.
20. Markland, F. S. and Smith, E. L., "Subtilisins: Primary Structure, Chemical and Physical Properties" in: Boyer, P. D., *The Enzymes*, vol. 3 (New York, Academic Press, 1971), pp. 561–608.
21. Waller, M. and Normansell, D. E., "The Hydrolysis of Human IgG with Subtilisin" *American Journal of Clinical Pathology*, vol. 31 (1975) pp. 358–364.
22. Rothgeb, T. M., et al, op. cit.
23. Agarwal, M. K., Yunginger, M. D., Swanson, M. C., Reed, C. E., "An Immunochemical method to Measure Atmospheric Allergens" *Journal Allergy and Clinical Immunology*, vol. 68, no. 3 (1981) pp. 194–200.
24. Fulwiler, R. D., op. cit.
25. Rothgeb, T. M., op. cit.
26. Agarwal, M. K. et al, (1981) op. cit.
27. Wells, J. D., et al, op. cit.
28. Agarwal, M. K., Ingram, J. W., Dunnette, S. and Gleich, G. J., "Immunochemical Quantitation of an Airborne Proteolytic Enzyme, Esperase®, in a Consumer Products Factory" *American Industrial Hygiene Association Journal*, vol. 47, no. 2 (1986), pp. 138–143.
29. Swanson, M. C., et al., op. cit.
30. Miller, L. S., Moore, V. S., Wardwell, A. L. and Smith, L. A. "Inhibition Enzyme Immunoassay for the Detection of Airborne Detergent Enzymes Causing Occupational Allergy." *Developments in Industrial Microbiology*, vol. 31 (1990), pp. 213–219.
31. Lowry O. H., Rosebrough, N. J., Farr, A. L. and Randall, R. J., "Protein Measurement with the Folin Phenol Reagent." *Journal of Biological Chemistry*, vol. 193, (1951) pp. 265–275.
32. Peters, T., "Serum Albumin." in: Anfinsen, B., Edsall, J. T. and Richards, F. M., *Advances in Protein Chemistry*, vol. 37, (New York, Academic Press, 1985), pp. 161–245.
33. Lowry, O. H., et al., op. cit.
34. Rothgeb, T. M., op. cit.
35. Voller, A., Bartlett, A., and Bidwell, D. E., "Enzyme Immunoassays with Special Reference to ELISA Techniques" *Journal of Clinical Pathology*, vol. 31 (1978), pp. 507–520.
36. Voller, A. et al., op. cit.
37. Voller, A. et al., op. cit.

We claim:

1. A method for determining a specific airborne allergen comprising:
   a) eluting a sample portion from a collected sample to a liquid medium;
   b) providing at least one stabilizing reagent to said sample portion with said stabilizing reagent selected from the group of stabilizing reagents consisting of enzyme stabilizing reagents, oxidizing agent neutralizing reagents, and antimicrobial reagents;
   c) providing reagents of a given concentration and controlling the temperature of said reagents and said stabilized sample portion at a temperature below room temperature;
   d) transferring a given amount of said stabilized sample portion to a reaction site having a given amount of an insolubilized substance that is obtained by insolubilizing an antibody substance which specifically binds to a specific airborne allergen to be determined, said step of insolubilizing said antibody substance comprising the steps of:
      1) adding said antibody substance to said reaction site in a buffer solution;
      2) incubating said antibody substance containing buffer solution at a temperature below room temperature to insolubilize said antibody substance by attaching to said reaction site; and
      3) removing unattached antibodies from said reaction site;
      4) adding an overcoat solution to said reaction site after said step of removing said unbound antibodies from said reaction site;
      5) incubating said overcoat solution;
      6) removing excess overcoat solution from said reaction site;
      7) drying said reaction site in a desiccator at a temperature below room temperature, said desiccator comprising:
         a) a sealed chamber;
         b) a pump for circulating air through said chamber in a closed loop with a monitored pressure differential between the outside environment and said chamber of about zero to about two inches of water;
         c) a drying agent located in said closed loop; and
         d) a port for placing said reaction site in and removing said reaction site from said chamber;
   e) reacting said stabilized sample portion with said insolubilized antibody substance for a given time at a temperature greater than room temperature to bind said specific airborne allergen in said stabilized sample with said insolubilized antibody substance;
   f) transferring to said reaction site a given amount of a labeled substance that is obtained by labeling a substance which specifically binds to said specific airborne allergen with a labeling agent;
   g) reacting said labeled substance with said bound specific airborne allergen for a given time and at a temperature greater than room temperature to bind said labeled substance with said bound specific airborne allergen;
   h) removing unbound labeled substance from said reaction site; and
   i) measuring an amount of labeled substance bound with said specific airborne allergen as a means of determining said specific airborne allergen.

2. The method of claim 1 with said labeling agent being an enzyme and with said step of measuring the amount of labeled substance bound with said specific airborne allergen comprising the steps of:
   a) transferring to said reaction site a given amount of a substrate reactive with said enzyme of said labeled substance;
   b) reacting said substrate with said enzyme of said labeled substance for a given time and at a temperature greater than room temperature to form a colored reaction product;
   c) stopping said reaction of said substrate with said enzyme of said labeled substance after a given time;
   d) measuring said colored reaction product;
   e) comparing measured colored reaction product with measured colored product formed when known amounts of a known specific airborne allergen are substituted for said sample portion in said specific airborne allergen determining method.

3. The method of claim 2 wherein
   a) said times and temperatures of
      1) said reaction of said stabilized sample portion with said insolubilized antibody substance,
      2) said reaction of said labeled substance with said bound specific airborne allergen, and
      3) said reaction of said substrate with said enzyme;
   b) said concentrations, amounts and temperatures of
      1) said reagents, and
      2) said known specific allergen; and
   c) said temperature and amount of said sample portion are controlled to allow all steps in said method to be completed in less than four and one half hours.

4. The method of claim 3 with an intra- or inter-assay precision having a coefficient of variation of less than 10%.

5. The method of claim 3 with an intra- or inter-assay precision having a coefficient of variation of less than 7%.

6. The method of claim 3 with an intra- or inter-assay precision having a coefficient of variation of less than 5%.

7. The method of claim 3 with an assay accuracy of 100±30%.

8. The method of claim 3 with an assay accuracy of 100±10%.

9. The method of claim 3 with an assay accuracy of 100±2%.

10. The method of claim 3 with a detection limit of 0.2 ng/mL.

11. The method of claim 3 with a standard curve response range of 0.2-20 ng/mL.

12. The method of claim 1 wherein said specific airborne allergen is an enzyme.

13. The method of claim 2 wherein said specific airborne allergen is an enzyme.

14. The method of claim 13 wherein said enzyme is an enzyme used in a detergent.

15. The method of claim 13 wherein said enzyme is an enzyme selected from the group of enzymes consisting of proteases, carbohydrases, and oxidases.

16. The method of claim 15 wherein said enzyme is an alkaline protease.

17. The method of claim 13 wherein said enzyme is selected from the group of enzymes consisting of Subtilisin Carlsberg, Subtilisin BPN', Cellulase, and Savinase.

18. The method of claim 1 wherein said antibody substance that is specifically bindable with a specific allergen is an antibody.

19. The method of claim 18 wherein said antibody is purified by affinity chromatography.

20. The method of claim 1 wherein said labeling agent is selected from the group of labeling agents consisting of radioisotope, enzyme, chemiluminescent, phosphorescent, infrared emitting and fluorescent material.

21. The method of claim 1 wherein said labeling agent is an enzyme.

22. The method of claim 21 wherein said enzyme is selected from the group of enzymes consisting of horseradish peroxidase, alkaline phosphatase, β-D-galactosidase, urease, acetyl cholinesterase, and glucose oxidase.

23. The method of claim 2 wherein said enzyme is selected from the group of enzymes consisting of horseradish peroxidase, alkaline phosphatase, β-D-galactosidase, urease, acetyl cholinesterase and glucose oxidase.

24. The method of claim 2 wherein said labeling agent is alkaline phosphatase and said substrate is para-nitrophenyl phosphate.

25. The method of claim 1 wherein said sample portion is provided with a given amount of sample preparation buffer.

26. The method of claim 25 wherein said sample preparation buffer comprises an enzyme stabilizing reagent, an oxidizing agent neutralizing reagent, and an antimicrobial reagent and has a pH of 7-10 and an ionic strength of 150-1000 mM.

27. The method of claim 25 wherein said sample preparation buffer comprises sodium chloride, Tris, BSA, sodium thiosulfate, calcium chloride, Tween and sodium azide.

28. The method of claim 1 wherein said eluting step and said step of providing a stabilizing reagent are carried out simultaneously.

29. The method of claim 1 wherein a given amount of buffer solution is added to said reaction site prior to heating of said reaction site.

30. The method of claim 1 with said desiccator further comprising:
   a) a rack mounted in said container for supporting said reaction site;
   b) inlets and outlets for distributing said circulating air through said container; and
   c) at least two valves located in said closed loop for isolating said drying agent from said sealed chamber.

31. The method of claim 30 with said desiccator constructed in a manner to allow stacking of one desiccator on another.

32. The method of claim 1 wherein:
   a) a programmable computer is used for controlling said time and said amount of reagents and sample in said allergen determining steps;
   b) a liquid handling system is controlled by said computer for transferring reagents and sample to said reaction site and removing materials from said reaction site;
   c) a cooler is used for maintaining said sample and said reagents at said temperature below room temperature;
   d) a heater is used for heating and maintaining said reaction sites at said temperature greater than room temperature; and
   e) a reader is used for determining said amount of labeled substance bound with said specific allergen.

* * * * *